US008956298B2

(12) United States Patent
Lee et al.

(10) Patent No.: US 8,956,298 B2
(45) Date of Patent: Feb. 17, 2015

(54) PROVIDING AN ULTRASOUND SPATIAL COMPOUND IMAGE IN AN ULTRASOUND SYSTEM

(75) Inventors: Suk Jin Lee, Seoul (KR); Jung Kim, Seoul (KR)

(73) Assignee: Samsung Medison Co., Ltd., Hongcheon-Gun, Gangwon-Do (KR)

( * ) Notice: Subject to any disclaimer, the term of this patent is extended or adjusted under 35 U.S.C. 154(b) by 988 days.

(21) Appl. No.: 12/962,289

(22) Filed: Dec. 7, 2010

(65) Prior Publication Data

US 2011/0137171 A1 Jun. 9, 2011

(30) Foreign Application Priority Data

Dec. 9, 2009 (KR) .................. 10-2009-0121590

(51) Int. Cl.
*A61B 8/00* (2006.01)
*G01S 15/89* (2006.01)
(Continued)

(52) U.S. Cl.
CPC ........... *G01S 15/8993* (2013.01); *A61B 8/5215* (2013.01); *A61B 8/085* (2013.01); *A61B 8/5253* (2013.01); *G06T 7/0012* (2013.01); *G01S 7/52074* (2013.01); *A61B 8/469* (2013.01);
(Continued)

(58) Field of Classification Search
None
See application file for complete search history.

(56) References Cited

U.S. PATENT DOCUMENTS 6,283,918 B1 9/2001 Kanda et al.

6,755,787 B2 * 6/2004 Hossack et al. ............... 600/447
(Continued)

FOREIGN PATENT DOCUMENTS

JP 11-164833 6/1999
JP 2007-125179 A 5/2007
(Continued)

OTHER PUBLICATIONS

Korean Office Action issued in Korean Patent Application No. 10-2009-121590 dated Dec. 28, 2011.
(Continued)

*Primary Examiner* — Unsu Jung
*Assistant Examiner* — Amanda Lauritzen Moher
(74) *Attorney, Agent, or Firm* — McDermott Will & Emery LLP (57) ABSTRACT

Embodiments for providing an ultrasound spatial compound image are disclosed. In one embodiment, by way of non-limiting example, an ultrasound system comprises: an ultrasound data acquisition unit configured to transmit and receive ultrasound signals to and from a target object to output first ultrasound data and a plurality of sets of second ultrasound data corresponding to a region of interest (ROI); a user input unit configured to receive input information for defining the ROI; and a processing unit in communication with the ultrasound data acquisition unit and the user input unit, the processing unit being configured to form volume data based on the plurality of sets of second ultrasound data, compare the first ultrasound data with the volume data to detect geometric information therein, form a two-dimensional (2D) ultrasound image based on the first ultrasound data, and a first three-dimensional (3D) ultrasound image and a second 3D ultrasound data based on the volume data in consideration of the geometric information, and perform a spatial compound upon the 2D ultrasound image, the first 3D ultrasound image and the second 3D ultrasound image based on the geometric information to form an ultrasound spatial compound image.

11 Claims, 5 Drawing Sheets

(51) Int. Cl.
    *A61B 8/08* (2006.01)
    *G06T 7/00* (2006.01)
    *G01S 7/52* (2006.01)
    *A61B 8/13* (2006.01)

(52) U.S. Cl.
    CPC .............. *A61B8/13* (2013.01); *G01S 7/52063* (2013.01); *G01S 7/52071* (2013.01)
    USPC .......................................... 600/443; 382/128

(56) References Cited

U.S. PATENT DOCUMENTS 8,157,737 B2 * 4/2012 Zhang et al. .................. 600/443
2003/0097068 A1 * 5/2003 Hossack et al. ............... 600/443
2009/0306508 A1 12/2009 Yoshida et al.

FOREIGN PATENT DOCUMENTS

| | | | |
|---|---|---|---|
| JP | 2009-101204 A | 5/2009 | |
| JP | 2010-17537 A | 1/2010 | |
| KR | 10-2009-0106107 | 10/2009 | |

OTHER PUBLICATIONS

Japanese Office Action issued in corresponding Japanese Application No. 2010-270751, dated Jul. 1, 2014, with English translation.

* cited by examiner

PROVIDING AN ULTRASOUND SPATIAL COMPOUND IMAGE IN AN ULTRASOUND SYSTEM

CROSS-REFERENCE TO RELATED APPLICATIONS

The present application claims priority from Korean Patent Application No. 10-2009-0121590 filed on Dec. 9, 2009, the entire subject matter of which is incorporated herein by reference.

TECHNICAL FIELD

The present disclosure generally relates to ultrasound systems, and more particularly to providing an ultrasound spatial compound image of two-dimensional and three-dimensional ultrasound images in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional (2D) or three-dimensional (3D) ultrasound images of internal features of an object (e.g., human organs).

The ultrasound system may provide the 3D ultrasound image including clinical information such as spatial information and anatomical figures of the target object, which cannot be provided by the 2D ultrasound image. The ultrasound system may transmit ultrasound signals into the target object and receive ultrasound echo signals reflected from the target object. The ultrasound system may further form the 2D ultrasound image based on the ultrasound echo signals. The ultrasound system may further transmit ultrasound signals into the target object and receive ultrasound echo signals reflected from the target object. The ultrasound system may further form volume data corresponding to a region of interest (ROI) defined in the 2D ultrasound image based on the ultrasound echo signals. The ultrasound system may further render the volume data to thereby form the 3D ultrasound image. However, it may be difficult to precisely comprehend a correlation between the 2D ultrasound image and the 3D ultrasound image.

SUMMARY

Embodiments for providing a plurality of slice images in an ultrasound system are disclosed herein. In one embodiment, by way of non-limiting example, an ultrasound system comprises: an ultrasound data acquisition unit configured to transmit and receive ultrasound signals to and from a target object to output first ultrasound data and a plurality of sets of second ultrasound data corresponding to a region of interest (ROI); a user input unit configured to receive input information for defining the ROI; and a processing unit in communication with the ultrasound data acquisition unit and the user input unit, the processing unit being configured to form volume data based on the plurality of sets of second ultrasound data, compare the first ultrasound data with the volume data to detect geometric information therein, form a two-dimensional (2D) ultrasound image based on the first ultrasound data, and a first three-dimensional (3D) ultrasound image and a second 3D ultrasound data based on the volume data in consideration of the geometric information, and perform a spatial compound upon the 2D ultrasound image, the first 3D ultrasound image and the second 3D ultrasound image based on the geometric information to form an ultrasound spatial compound image.

In another embodiment, there is provided a method of providing an ultrasound spatial compound image, comprising: a) acquiring first ultrasound data for forming a two-dimensional (2D) ultrasound image indicative of a target object; b) acquiring a plurality of sets of second ultrasound data to form volume data corresponding to the target object; c) comparing the first ultrasound data with the volume data to detect geometric information therein; d) forming the 2D ultrasound image based on the first ultrasound data, and a first three-dimensional (3D) ultrasound image and a second 3D ultrasound image based on the volume data in consideration of the geometric information; and e) performing a spatial compound upon the 2D ultrasound image, the first 3D ultrasound image and the second 3D ultrasound image based on the geometric information to form an ultrasound spatial compound image.

In yet another embodiment, there is provided a computer readable medium comprising computer executable instructions configured to perform the following acts: a) acquiring first ultrasound data for forming a two-dimensional (2D) ultrasound image indicative of a target object; b) acquiring a plurality of sets of second ultrasound data to form volume data corresponding to the target object; c) comparing the first ultrasound data with the volume data to detect geometric information therein; d) forming the 2D ultrasound image based on the first ultrasound data, and a first three-dimensional (3D) ultrasound image and a second 3D ultrasound image based on the volume data in consideration of the geometric information; and e) performing a spatial compound upon the 2D ultrasound image, the first 3D ultrasound image and the second 3D ultrasound image based on the geometric information to form an ultrasound spatial compound image.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
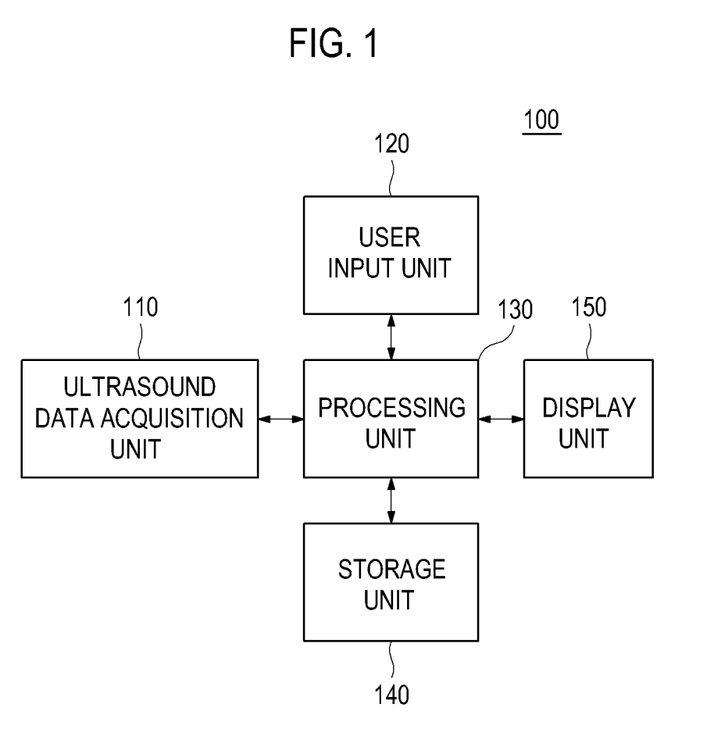
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include an ultrasound data acquisition unit 110. The ultrasound data acquisition unit 110 may be configured to transmit and receive ultrasound signals to and from a target object to output ultrasound data.

Figure 2:
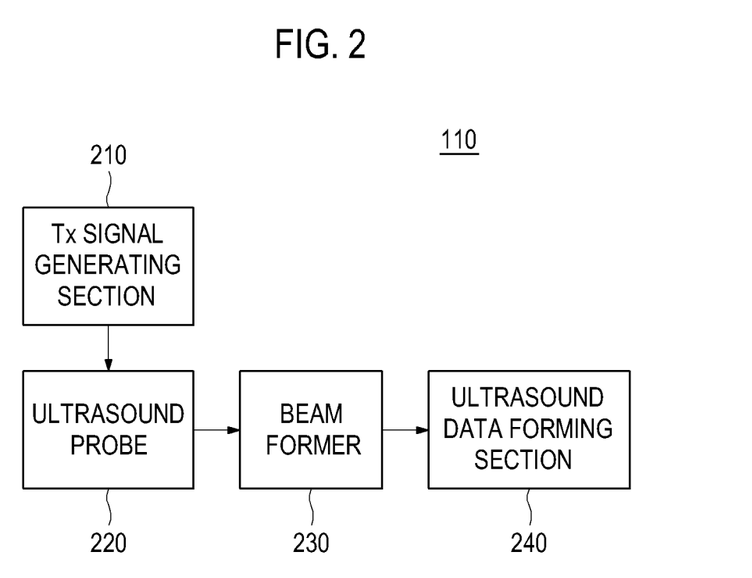
FIG. 2 is a block diagram showing an illustrative embodiment of an ultrasound data acquisition unit.

FIG. 2 is a block diagram showing an illustrative embodiment of the ultrasound data acquisition unit 110. Referring to FIG. 2, the ultrasound data acquisition unit 110 may include a transmit (Tx) signal generating section 210, an ultrasound probe 220, a beam former 230 and an ultrasound data forming section 240.

The Tx signal generating section 210 may be configured to generate Tx signals. In one embodiment, the Tx signal generating section 210 may generate first Tx signals for obtaining a frame corresponding to a two-dimensional (2D) ultrasound image indicative of the target object. The Tx signal generating section 210 may further generate a plurality of sets of second Tx signals for obtaining a plurality of frames $F_i$ ($1 \leq i \leq N$) corresponding to a three-dimensional (3D) ultrasound image at every predetermined time, as shown in FIG. 3.

Figure 3:
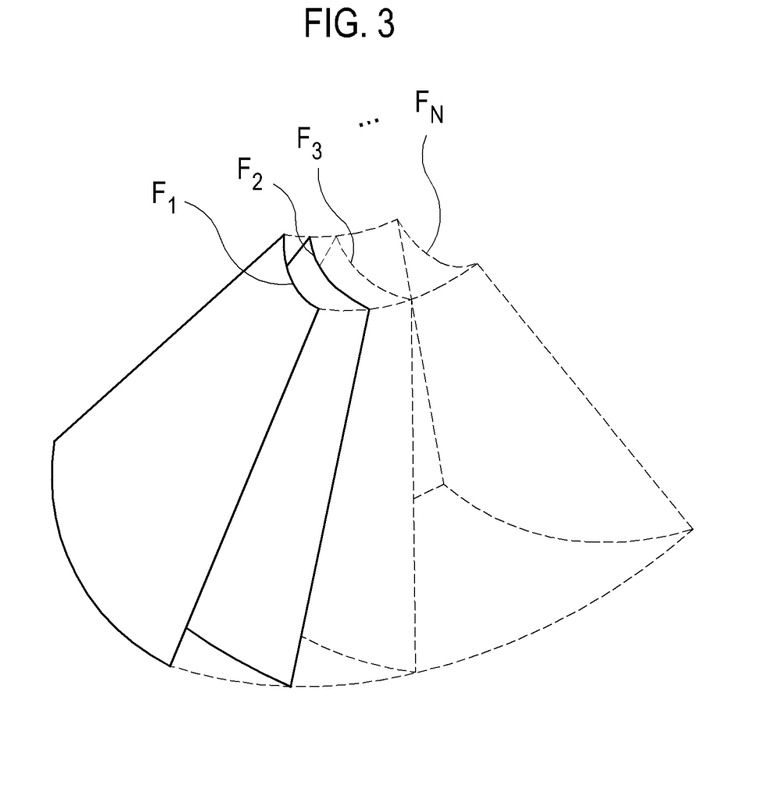
FIG. 3 is a schematic diagram showing an example of acquiring ultrasound data corresponding to a plurality of frames.

FIG. 3 is a schematic diagram showing an example of acquiring ultrasound data corresponding to the plurality of frames $F_i$ ($1 \leq i \leq N$). The plurality of frames $F_i$ ($1 i \leq N$) may represent sectional planes of the target object (not shown).

Referring back to FIG. 2, the ultrasound probe 220 may include a plurality of elements (not shown) for reciprocally converting between ultrasound signals and electrical signals. The ultrasound probe 220 may be configured to transmit and receive ultrasound signals to and from the target object to output received signals. The received signals may be analog signals. The ultrasound probe 220 may include a three-dimensional (3D) mechanical probe, a two-dimensional (2D) array probe and the like. However, it should be noted herein that the ultrasound probe 220 may not be limited thereto.

In one embodiment, the ultrasound probe 220 may transmit ultrasound signals into the target object in response to the first Tx signals provided from the Tx signals generating section 210. The ultrasound probe 220 may further receive ultrasound echo signals reflected from the target object to thereby output first received signals to form a 2D ultrasound image. The ultrasound probe 220 may further transmit ultrasound signals into the target object in response to the second Tx signals provided from the Tx signal generating section 210. The ultrasound probe 220 may further receive ultrasound echo signals reflected from the target object to thereby output second received signals to form volume data.

The beam former 230 may be configured to convert the received signals provided from the ultrasound probe 220 into digital signals. The beam former 230 may further apply delays to the digital signals in consideration of distances between the elements and focal points to thereby output digital receive-focused signals.

In one embodiment, the beam former 230 may convert the first received signals provided from the ultrasound probe 220 into first digital signals. The beam former 230 may further apply delays to the first digital signals in consideration of the distances between the elements and the focal points to thereby output first digital receive-focused signals. The beam former 230 may further convert the second received signals provided from the ultrasound probe 220 into second digital signals. The beam former 230 may further apply delays to the second digital signals in consideration of the distances between the elements and the focal points to thereby output second digital receive-focused signals.

The ultrasound data forming section 240 may be configured to form ultrasound data based on the digital receive-focused signals. The ultrasound data forming section 240 may further perform various signal processing (e.g., gain adjustment) upon the digital receive-focused signals.

In one embodiment, the ultrasound data forming section 240 may form first ultrasound data based on the first digital receive-focused signals. The first ultrasound data may be stored in a storage unit 140 in FIG. 1. The ultrasound data forming section 240 may further form a plurality of sets of second ultrasound data corresponding to the plurality of frames $F_i$ ($1 \leq i \leq N$) based on the plurality of second digital receive-focused signals provided from the beam former 230. The plurality of sets of second ultrasound data may be stored in the storage unit 140 shown in FIG. 1.

Referring back to FIG. 1, the ultrasound system 100 may further include a user input unit 120. The user input unit 120 may be configured to receive input information from a user. In one embodiment, the input information may include first input information for defining a region of interest (ROI), as well as second input information for rotating an ultrasound spatial compound image. The user input unit 120 may include a control panel, a mouse, a keyboard and the like. However, it should be noted herein that the user input unit 120 may not be limited thereto.

The ultrasound system 100 may further include a processing unit 130 in communication with the ultrasound data acquisition unit 110 and the user input unit 120. The processing unit 130 may include a central processing unit, a microprocessor, a graphic processing unit and the like. However, it should be noted herein that the processing unit 130 may not be limited thereto.

Figure 4:
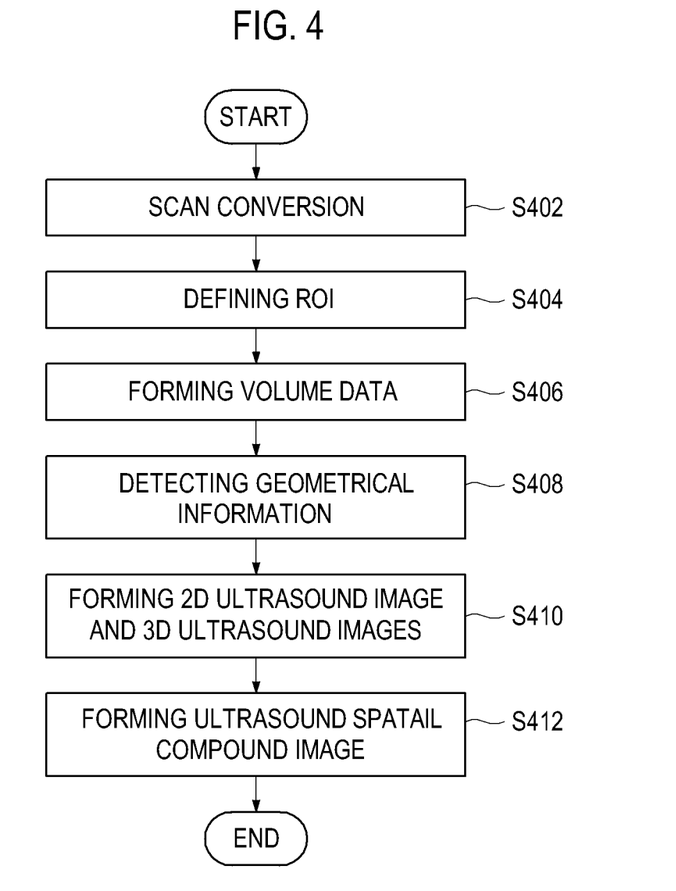
FIG. 4 is a flow chart showing a process of forming an ultrasound spatial compound image.

FIG. 4 is a flow chart showing a process of forming the ultrasound spatial compound image. The processing unit 130 may be configured to perform a scan-conversion upon the first ultrasound data formed by the ultrasound data forming section 240 to form an ultrasound image, at step 402 in FIG. 4.

The processing unit 130 may be configured to define the ROI in the ultrasound image based on the input information (i.e., first input information) provided from the user input unit 120, at step S404 in FIG. 4.

Figure 5:
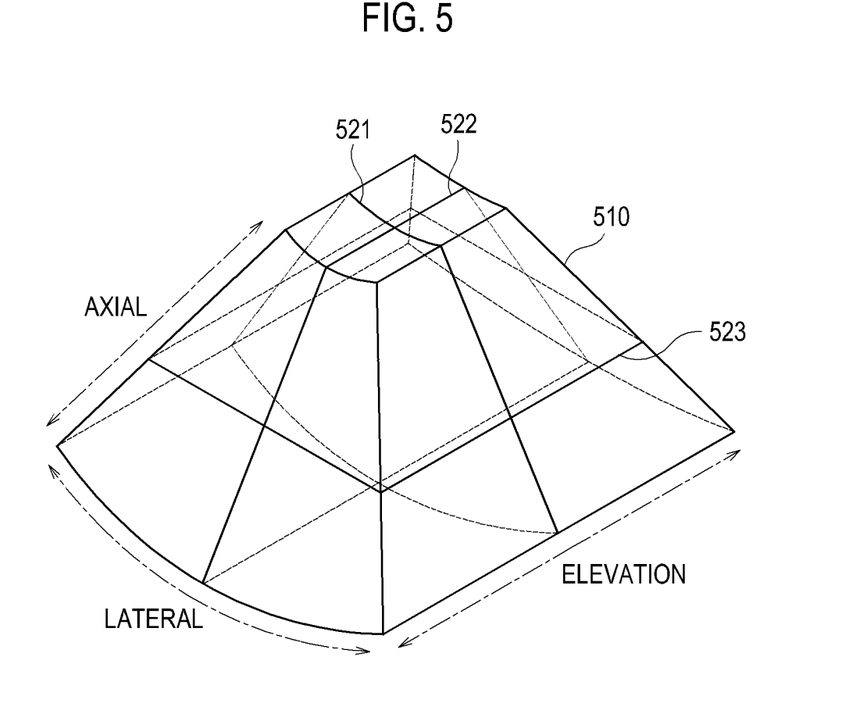
FIG. 5 is a schematic diagram showing an example of volume data.

The processing unit 130 may be configured to synthesize the plurality of sets of second ultrasound data corresponding to the plurality of frames $F_i$ ($1 \leq i \leq N$) to thereby form volume data 510 as shown in FIG. 5, at step S406 in FIG. 4. The volume data may be stored in the storage unit 140 as shown in FIG. 1.

FIG. 5 is a schematic diagram showing an example of the volume data 510. The volume data 510 may include a plurality of voxels (not shown) having brightness values. In FIG. 5, reference numerals 521 to 523 represent an A plane, a B plane and a C plane. The A plane 521, the B plane 522 and the C plane 523 may be mutually orthogonal. Also, in FIG. 5, the axial direction may be a Tx direction of the ultrasound signals, the lateral direction may be a longitudinal direction of the elements, and the elevation direction may be a swing direction of the elements, i.e., a depth direction of the 3D ultrasound image.

The processing unit 130 may be configured to compare the first ultrasound data with the volume data 510 to detect geometric information therein, at step S408 in FIG. 4. In one embodiment, the processing unit 130 may detect similarities between the first ultrasound data and each of the second ultrasound data. The processing unit 130 may further compare the similarities to detect a maximum similarity. The processing unit 130 may further detect a position of second ultrasound data corresponding to the maximum similarity from the volume data 510. The processing unit 130 may further set the detected position as the geometric information between the first ultrasound data and the volume data 510.

The processing unit 130 may be configured to form a two-dimensional (2D) ultrasound image based on the first ultrasound data, and 3D ultrasound images based on the volume data 510 in consideration of the geometric information, at step S410 in FIG. 4.

Figure 6:
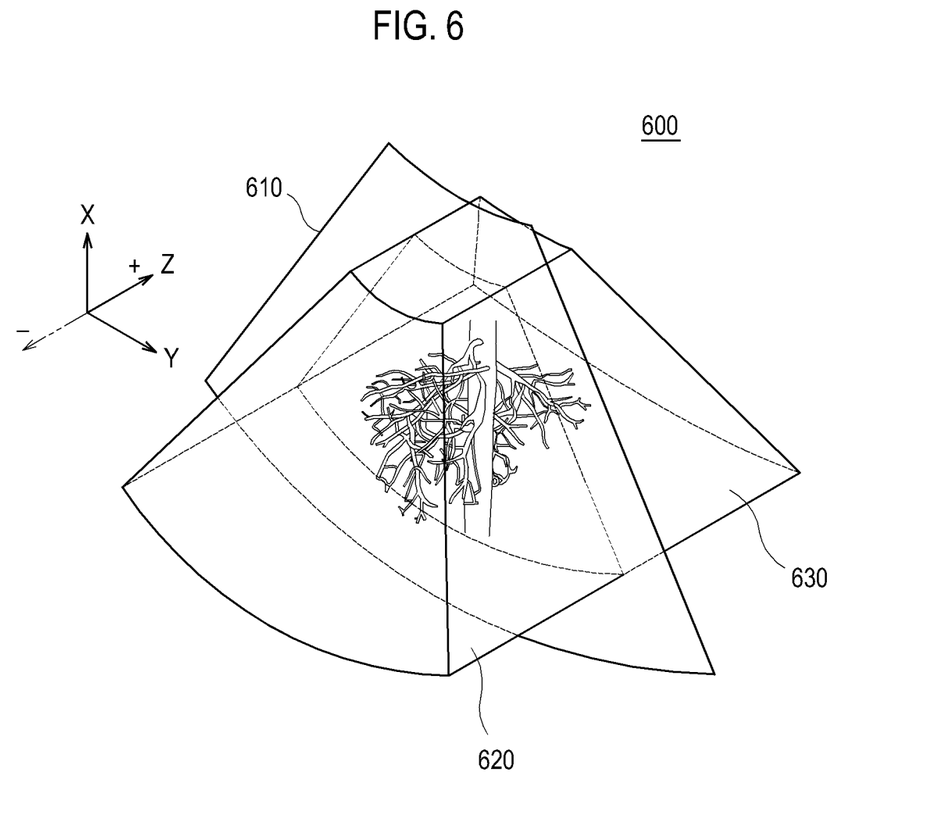
FIG. 6 is a schematic diagram showing an example of an ultrasound spatial compound image.

In one embodiment, the processing unit 130 may perform the scan conversion upon the first ultrasound data to form the 2D ultrasound image 610 as shown in FIG. 6. The processing unit 130 may further extract a portion of the volume data 510 corresponding to a first region, which is located on a front of the geometric information in the elevation direction (i.e., −z direction as shown in FIG. 6) of the volume data 510. The processing unit 130 may further render the extracted portion of the volume data 510 corresponding to the first region to form a 3D ultrasound image ("a first 3D ultrasound image") 620 as shown in FIG. 6. The processing unit 130 may further perform a color rendering upon the extracted portion of the volume data 510. The methods of performing the color rendering are well known in the art. Thus, they have not been described in detail so as not to unnecessarily obscure the present invention. The processing unit 130 may further perform an alpha blending processing upon the first 3D ultrasound image 620 to set a transparency of the first 3D ultrasound image 620. The processing unit 130 may further extract the remaining portion of the volume data 510 corresponding to a second region, which is located on a back of the geometric information in the elevation direction (i.e., +z direction as shown in FIG. 6) of the volume data 510. The processing unit 130 may further render the extracted remaining portion of the volume data 510 corresponding to the second region to form a 3D ultrasound image ("a second 3D ultrasound image") 630 as shown in FIG. 6. The processing unit 130 may further perform a color rendering upon the extracted remaining portion of the volume data 510. The processing unit 130 may further perform an alpha blending processing upon the second 3D ultrasound image 630 to set a transparency of the second 3D ultrasound image 630.

The processing unit 130 may be configured to perform a spatial compound upon the 2D ultrasound image 610 and the 3D ultrasound images 620 and 630 to form the ultrasound spatial compound image 600 as shown in FIG. 6, at step S412 in FIG. 4.

Optionally, the processing unit 130 may further rotate the ultrasound spatial compound image 600 based on the input information (i.e., second input information) provided from the user input unit 120.

Referring back to FIG. 1, the ultrasound system 100 may further include the storage unit 140. The storage unit 140 may store the first ultrasound data and the plurality of sets of second ultrasound data acquired from the ultrasound data acquisition unit 110. The storage unit 140 may further store the volume data 510 formed by the processing unit 130.

The ultrasound system 100 may further include a display unit 150. The display unit 150 may display the 2D ultrasound image formed by the processing unit 130. The display unit 150 may further display the ultrasound spatial compound image formed by the processing unit 130. The display unit 150 may further display the 3D ultrasound images formed by the processing unit 130.

In another embodiment, the present invention may provide a computer readable medium comprising computer executable instructions configured to perform the following acts: a) acquiring first ultrasound data for forming a two-dimensional (2D) ultrasound image indicative of a target object; b) acquiring a plurality of sets of second ultrasound data to form volume data corresponding to the target object; c) comparing the first ultrasound data with the volume data to detect geometric information therein; d) forming the 2D ultrasound image based on the first ultrasound data, and a first three-dimensional (3D) ultrasound image and a second 3D ultrasound image based on the volume data in consideration of the geometric information; and e) performing a spatial compound upon the 2D ultrasound image, the first 3D ultrasound image and the second 3D ultrasound image based on the geometric information to form an ultrasound spatial compound image. The computer readable medium may comprise a floppy disk, a hard disk, a memory, a compact disk, a digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound data acquisition unit including a probe comprising a plurality of elements for converting between ultrasound signals and electrical signals and configured to transmit and receive ultrasound signals to and from a target object, and configured to form first ultrasound data and a plurality of sets of second ultrasound data using the received ultrasound signals;
a processing unit connected to the probe, the processing unit being configured to form a two-dimensional (2D) ultrasound image based on the first ultrasound data; and
a user input unit including a user interface connected to the processing unit and configured to receive input information for defining a region of interest (ROI) in the 2D ultrasound image,
wherein the processing unit is configured to form volume data based on the plurality of sets of the second ultrasound data corresponding to the ROI, compare the first ultrasound data with the volume data to detect geometric information including a position in the volume data, form a first three-dimensional (3D) ultrasound image corresponding to a first region which is located on a front, relative to an elevation direction of the 3D data, of the 2D ultrasound image and a second 3D ultrasound image corresponding to a second region which is located on a back, relative to an elevation direction of the 3D data, of the 2D ultrasound image based on the volume data in consideration of the geometric information, and perform a spatial compound upon the 2D ultrasound image, the first 3D ultrasound image and the second 3D ultrasound image based on the geometric information to form an ultrasound spatial compound image.

2. The ultrasound system of claim 1, wherein the processing unit is configured to;
detect similarities between the first ultrasound data and each of the second ultrasound data;
compare the similarities to detect a maximum similarity;
detect a position of second ultrasound data corresponding to the maximum similarity from the volume data; and set the detected position as the geometric information between the first ultrasound data and the volume data.

3. The ultrasound system of claim 1, wherein the processing unit is further configured to perform an alpha blending processing upon the first 3D ultrasound image and the second 3D ultrasound image.

4. The ultrasound system of claim 1, wherein the processing unit is configured to:
extract a portion of the volume data corresponding to the first region;
render the extracted portion of the volume data corresponding to the first region to form the first 3D ultrasound image;
extract a remaining portion of the volume data corresponding to the second region; and
render the extracted remaining portion of the volume data corresponding to the second region to form the second 3D ultrasound image.

5. The ultrasound system of claim 1, wherein the processing unit is further configured to perform a color rendering upon the extracted portion of the volume data corresponding to the first region and the extracted remaining portion of the volume data corresponding to the second region.

6. A method of providing an ultrasound spatial compound image, comprising:
a) acquiring first ultrasound data for forming a two-dimensional (2D) ultrasound image indicative of a target object via a probe;
b) acquiring a plurality of sets of second ultrasound data via the probe;
c) receiving input information for defining a region of interest (ROI) in the 2D ultrasound image;
d) forming volume data based on the plurality of sets of the second ultrasound data corresponding to the ROI;
e) comparing, via a processing unit connected to the probe, the first ultrasound data with the volume data to detect geometric information including a position in the volume data;
f) forming, via the processing unit, a first three-dimensional (3D) ultrasound image corresponding to a first region which is located on a front, relative to an elevation direction of the 3D data, of the 2D ultrasound image and a second 3D ultrasound image corresponding to a second region which is located on a back, relative to an elevation direction of the 3D data, of the 2D ultrasound image based on the volume data in consideration of the geometric information; and
g) performing a spatial compound, via the processing unit, upon the 2D ultrasound image, the first 3D ultrasound image and the second 3D ultrasound image based on the geometric information to form an ultrasound spatial compound image.

7. The method of claim 6, wherein the step e) comprises:
detecting similarities between the first ultrasound data and each of the second ultrasound data;
comparing the similarities to detect a maximum similarity;
detecting a position having the maximum similarity from the volume data; and
setting the detected position as the geometric information therein.

8. The method of claim 6, wherein the step f) comprises:
performing a scan conversion upon the first ultrasound data to form the 2D ultrasound data;
extracting a portion of the volume data corresponding to the first region;
rendering the extracted portion of the volume data corresponding to the first region to form the first 3D ultrasound image;
extracting a remaining portion of the volume data corresponding to the second region; and
rendering the extracted remaining portion of the volume data corresponding to the second region to form the second 3D ultrasound image.

9. The method of claim 8, wherein the step f) further comprises:
performing a color rendering upon the extracted portion of the volume data corresponding to the first region and the extracted remaining portion of the volume data corresponding to the second region.

10. The method of claim 8, wherein the step f) further comprises:
performing an alpha blending processing upon the first 3D ultrasound image and the second 3D ultrasound image.

11. A non-transitory computer readable medium comprising computer executable instructions configured to perform following acts:
a) acquiring first ultrasound data for forming a two-dimensional (2D) ultrasound image indicative of a target object;
b) acquiring a plurality of sets of second ultrasound data;
c) receiving input information for defining a region of interest (ROI) in the 2D ultrasound image;
d) forming volume data based on the plurality of sets of the second ultrasound data corresponding to the ROI;
e) comparing the first ultrasound data with the volume data to detect geometric information including a position in the volume data;
f) forming a first three-dimensional (3D) ultrasound image corresponding to a first region which is located on a front, relative to an elevation direction of the 3D data, of the 2D ultrasound image and a second 3D ultrasound image corresponding to a second region which is located on a back, relative to an elevation direction of the 3D data, of the 2D ultrasound image based on the volume data in consideration of the geometric information; and
g) performing a spatial compound upon the 2D ultrasound image, the first 3D ultrasound image and the second 3D ultrasound image based on the geometric information to form an ultrasound spatial compound image.

* * * * *